United States Patent [19]

Saunders et al.

[11] 4,018,685
[45] Apr. 19, 1977

[54] AUTOMATIC LIQUID MIXING DEVICE

[75] Inventors: Dennis L. Saunders, Anaheim; John C. Caldwell, Pomona, both of Calif.

[73] Assignee: Union Oil Company of California, Brea, Calif.

[22] Filed: Oct. 24, 1975

[21] Appl. No.: 625,577

[52] U.S. Cl. .......................... 210/141; 210/198 C; 137/565; 137/624.15
[51] Int. Cl.² ......................................... B01D 15/08
[58] Field of Search .......... 137/565, 624.15, 625.4, 137/625.41; 210/101, 198 C

[56] References Cited

UNITED STATES PATENTS

| | | | |
|---|---|---|---|
| 3,301,273 | 1/1967 | Monath | 137/624.15 |
| 3,446,057 | 5/1969 | Bakalyar | 210/198 C |
| 3,487,996 | 1/1970 | Lofgren | 137/624.15 X |

Primary Examiner—Robert G. Nilson
Attorney, Agent, or Firm—Richard C. Hartman; Dean Sandford; Gerald L. Floyd

[57] ABSTRACT

A device for mixing a plurality of liquid components in preselected proportions to form a mixture of the liquid components. The device includes a separate liquid component storage reservoir for each liquid component, a pump, means to successively connect the suction of the pump to each reservoir, and proportioning means to control the switching of the pump suction to each storage reservoir for a short, controlled time interval during each of a series of operating cycles which are repeated throughout the mixing operations.

21 Claims, 1 Drawing Figure

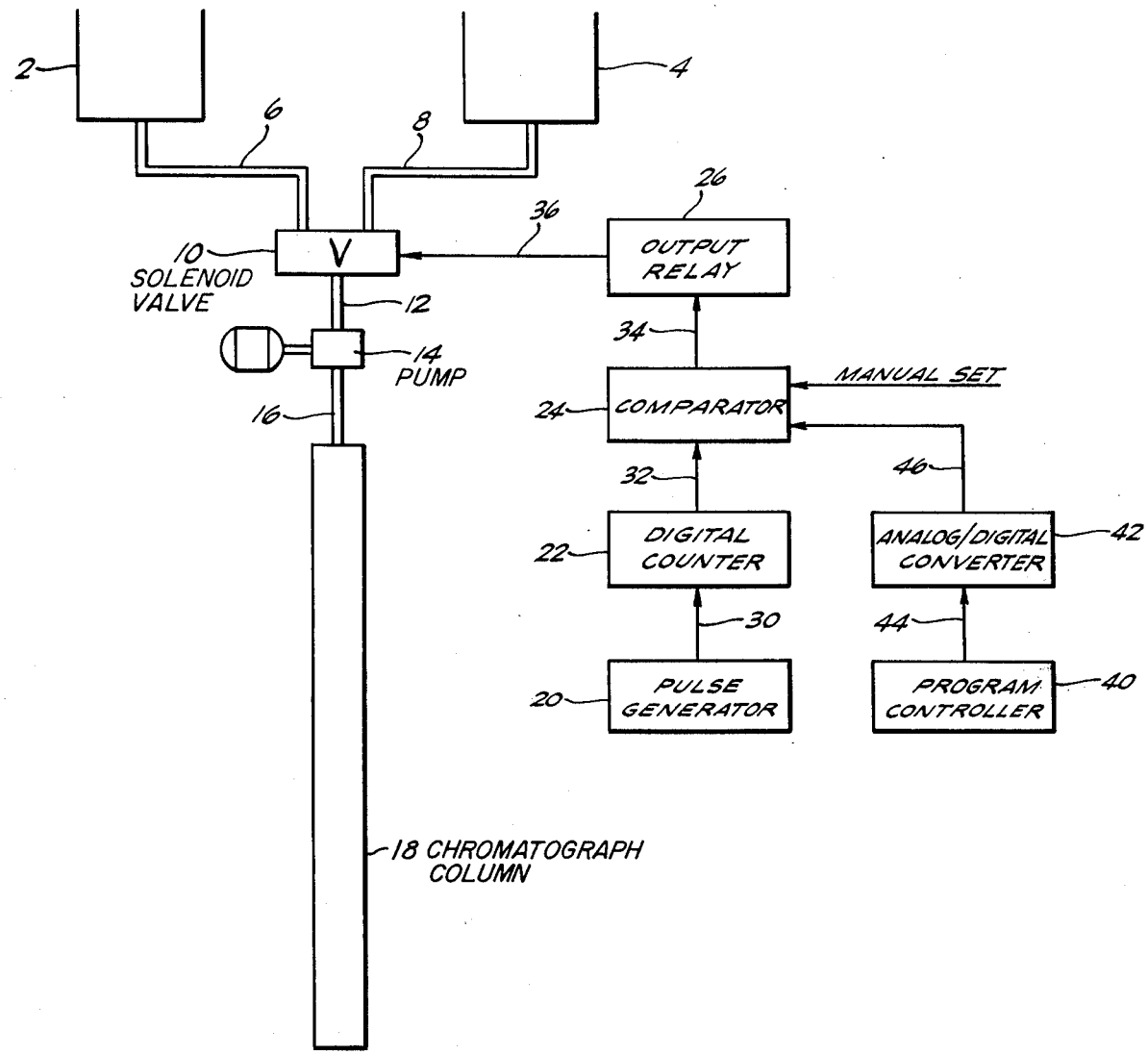

AUTOMATIC LIQUID MIXING DEVICE

BACKGROUND OF THE INVENTION

1. Field of the Invention

This invention relates to the mixing of liquids in controlled proportions, and more particularly to the mixing of liquid components in pre-selected proportions to provide a solvent for use in liquid chromatography.

2. Description of the Prior Art

Many operations require the use of various mixtures of two or more liquid components, and need exists for a device capable of mixing a plurality of liquid components in pre-selected proportions to form a mixture having a desired composition, and which permits ready adjustment of the selected proportions.

One particular application for such device is in the field of liquid chromatography. Chromatography is the technique of separating a mixture of chemical elements and/or compounds by passing a quantity, or slug, of the mixture to be separated in a continuous stream of mobile carrier phase, which can be a suitable gas or liquid, through an elongated bed of a solid absorbent material contained in a chromatograph column. As the chemical mixture is carried through the column by the mobile phase, the various constituents of the mixture are adsorbed and desorbed from the solid absorbent at different rates so that the various components will tend to separate in the column and exit the column at different times. This separation allows the components to be individually collected or identified by a suitable analytical procedure.

The solvents employed as the mobile carrier phase in liquid chromatography determine, in part, the rate at which the components of the mixture to be separated travel through the column. These solvents are often admixtures of two or more liquid components mixed in the proper proportions to provide a solvent of the desired composition. However, it is frequently the case that the optimum solvent composition cannot be predetermined. Consequently, it is often desirable to change the solvent composition between or during runs. Also, in gradient elution chromatography, the composition of the solvent is changed during the course of the elution. Thus, in many liquid chromatographic operations there must be provided a wide variety of multicomponent solvent mixtures containing different proportions of components. Hand mixing of the solvent compositions is laborious and time consuming.

Much effort has been expended in developing apparatus for admixing fluids in predetermined proportions. The devices disclosed in U.S. Pat. No. 3,647,002 to Lindsay and U.S. Pat. No. 3,693,653 to Cramer et al. are examples of such apparatus. Liquid proportioning devices for use in liquid chromatography are disclosed in U.S. Pat. No. 3,446,057 to Bakalyar et al.; in *Introduction to Modern Liquid Chromatography* by L. R. Snyder et al., Wiley-Interscience Publications, New York, N.Y., pages 110–119, (1974); and in articles by Scott, "Gradient Elution Facilities for LC Using the Continuous and Incremental Methods of Solvent Mixing", *Journal of Chromatographic Science*, Vol. 9, pages 385–389, (1971); by Stolyhwo et al., "Studies on the Analysis of Lipid Classes by Gradient Elution Adsorption Chromatography", *Journal of Chromatographic Science*, Vol. 11, pages 20–25, (1973); and by Byrne et al., "A Multifunctional Gradient Device for Use in High-Speed Liquid Chromatography", *Journal of Chromatographic Science*, Vol. 9, pages 592–595, October 1971. While these devices have met with varying success, need exists for a simple, low cost device capable of providing a continuous supply of a mixture of liquid components in varying pre-selected proportions.

Accordingly, a principal object of this invention is to provide an apparatus to admix a plurality of liquid components in controlled proportions to provide a solvent mixture having a desired composition.

Another object of this invention is to provide such an apparatus which is capable of readily changing the proportions of the liquid components to provide solvent mixtures of different pre-selected compositions.

A further object of the invention is to provide such an apparatus which is capable of continuously varying the proportions of said liquid components in said mixture in accordance with a predetermined program.

A still further object of this invention is to provide such an apparatus for use in conjunction with a liquid chromatograph to provide a continuous supply of solvent mixture having a predetermined composition for use as the mobile carrier phase.

Other objects, advantages and features of the invention will be apparent from the following description, drawing and appended claims.

DESCRIPTION OF THE PREFERRED EMBODIMENTS

Referring to the drawing, one embodiment of the invention useful in admixing various pre-selected proportions of two liquid components includes first and second liquid component reservoirs 2 and 4 adapted to separately contain the two liquid components. The liquid component reservoirs are connected to switching device 10 by the conduits 6 and 8, and switching device 10 is connected to the suction of pump 14 by conduit 12. The discharge of pump 14 is connected to a point of use, such as the inlet of chromatograph column 18, by conduit 16.

Switching device 10 can be any arrangement of valves or flow controls means that successively connects the suction of pump 14 to each of the liquid component reservoirs 2 and 4 and allows liquid component to separately flow from each of the successively connected liquid component reservoirs 2 and 4 to the pump suction, while preventing the liquid component from simultaneously flowing from the other reservoirs. In the case of the two-component mixing apparatus illustrated in the drawing, switching device 10 can be a conventional three-way solenoid valve having two inlets and a single outlet.

Pump 14 can be any type of pump capable of transferring the liquid component from the reservoirs to the point of use at the desired flow rate, and can be driven by any convenient means such as electric or fluid motors, and the like. In the case of a fluid mixing device adapted for use with a chromatograph, pump 14 is preferably a small, electric-motor driven constant volume reciprocating pump having either one or two pistons and a capacity of from about 0.1 to about 100 milliliters per minute.

Where a mixing receiver is not employed to collect the liquid components discharged from pump 14, and delivery of a mixed liquid product of uniform composition at the point of use is desired, it is preferred that the volume of liquid pumped during each operating cycle be small as compared to the combined fluid volume of the pump and the common connecting conduits 12 and 16, i.e., that the flow volume during each operating cycle be low as compared with the total mixed liquid system volume. This will assure that liquid components pumped during several operating cycles will be contained in the system to enhance mixing of liquid components and assure a product mixture of uniform composition. Preferably, the combined volume of liquid component pumped during each operating cycle is less than about 50 percent of the total system volume and more preferably less than about 25 percent of this volume to assure a residence time of at least about 2 operating cycles, and more preferably of at least about 4 operating cycles.

Referring again to the drawing, switching device 10 is actuated to shift the suction of pump 14 to the other of the liquid component reservoirs by the proportion control unit which includes pulse generator 20, digital counter 22, comparator 24 and output relay 26. A pulse signal is generated by pulse generator 20 to provide a clock signal for the timing control. This pulse signal is input to the digital counter which repetitively counts the number of pulses from 0 to a pre-selected fixed number, e.g., from 0 to 999, or some other arbitrary value. The number of pulses counted measures the length of each operating cycle, i.e., in a device that repetitively counts from 0 to 999, each operating cycle starts at the count of 0 and ends at the count of 999. The real time duration of each operating cycle is determined by the number of pulses selected as a measure of the operating cycle and the frequency of the pulse signal. For example, timer-pulses can be set from 0.001 millisecond to 999 seconds which permits the operating cycle time to be varied from 1 second to 277 hours. Operating cycle times of from about 0.1 to about 100 seconds are generally employed.

The portion of the time that the suction of pump 14 is connected to each reservoir is determined by comparator 24. A binary coded decimal output from digital counter 22 is inputted to comparator 24, which compares the input value, i.e., the number of pulses registered by digital counter 22 during the then current operating cycle, with a pre-selected index value set into the comparator. Upon attaining the count of 0, an output signal from comparator 24 will cause output relay 26 to actuate shift device 10 and shift the suction of pump 14 to the first liquid component storage reservoir. Then, upon reaching each pre-selected index value set into comparator 24, an output signal from comparator 24 activates output relay 26 and again actuates the shift device to cause the suction of pump 14 to be switched to another liquid component reservoir, the pump being shifted back to the first reservoir upon attaining a count of 0.

The various components forming the proportion control unit are conventional, commercially available electrical and electronic components.

Pulse generator 20 can be any device capable of generating a series of constant frequency electrical pulses, i.e., a constant frequency pulsed output signal having a frequency between about 100 and 100,000 Hertz. Preferably, the device is capable of adjustment to vary the output frequency to permit the real time span of the operating cycle to be changed. One conventional device for generating a pulsed output signal is a variable frequency square wave signal generator. Another conventional device that can be used is a variable frequency pulse timer. Alternately, fixed frequency components can be utilized and the mixing apparatus operated on a fixed time interval operating cycle, or other means can be provided to vary the length of the operating cycle. The output of pulse generator 20 is electrically connected to the input of digital counter 22 by means of conductor 30.

Digital counter 22 can be any conventional repeating-type digital counter having a binary coded decimal output, i.e., a digital counter of the type that counts from 0 to a fixed number and then resets to 0. A three digit counter capable of counting from 000 to 999 is particularly convenient for use in many applications.

The output of digital counter 22 is electrically connected to the input of comparator 24 by conductor 32, and the output of comparator 24 is electrically connected to output relay 26 by conductor 34. Output relay 26, conveniently a solid state relay, is electrically connected to switching device 10 by conductor 36. Comparator 24 continuously compares the number of pulses registered on digital counter 22 with a selected index value representative of an integer within the range of the counter, i.e., within the range of 0 to 999 in the case of a 0 to 999 counter. Comparator 24 detects when the input value is below the index value, in which event the suction of pump 14 is connected to the first of the liquid component reservoirs, and when the input value is equal to or above the index value causing an output signal to actuate relay 26 which in turn actuates the shifting of the pump suction to the other liquid component reservoir. In the case of apparatus for mixing more than two liquid components, comparator 24 must be capable of the setting of an additional index value for each additional component to be mixed, and of detecting when the input value is equal to the index value and outputting an appropriate signal to actuate relay 26.

The real time interval of each operating cycle can be determined as follows:

$$T = P/F$$

where

T is the time duration of each operating cycle in seconds;

P is the total number of pulses registered by the digital counter during each operating cycle (including the count of 0); and F is the frequency of the pulse signal.

The real time interval of each operating cycle during which each liquid component is pumped can be determined as follows:

$$T = T_1 + T_2 + --- T_n$$

$$T_{1,2,n} = PC_{1,2,n}$$

where $T_1$, $T_2$ and $T_n$ are the time intervals during which components 1, 2 and $n$, respectively, are pumped; and $C_1$, $C_2$ and $C_n$ are the volume proportion of components 1, 2 and $n$, respectively, of the product mixture expressed as decimal fractions.

The pumping of component 1 is initiated during each operating cycle at the count of 0, and pumping of the other components is initiated when the count equals the respective index value set into the comparator. The respective index values are determined as follows:

$$I_1 = 0$$

$$I_2 = I_1 + PC_1$$

$$I_n = I_1 + I_2 + --- PC_{n-1}$$

where $I_1$, $I_2$ and $I_n$ are the index values to be set into the comparator for each component 1, 2 and $n$.

The determination of the proper index values for an exemplary three component mixture containing 25 volume percent of component 1, 25 volume percent of component 2 and 50 volume percent of component 3 and using a mixing device having a 000 to 999 counter (a count of 1,000 pulses) and a pulse frequency of 100 pulses/second is illustrated as follows:

$$T = P/F = 1,000/100 = 10 \text{ seconds}$$

$$T_1 = TC_1 = 10 \times 0.25 = 2.5 \text{ seconds}$$

$$T_2 = TC_2 = 10 \times 0.25 = 2.5 \text{ seconds}$$

$$T_3 = TC_3 = 10 \times 0.50 \times 5.0 \text{ seconds}$$

$$I_1 = 0$$

$$I_2 = I_1 + PC_1 = 0 + 1,000 \times 0.25 = 250$$

$$I_3 = I_1 + I_2 + PC_2 = 0 + 250 + 1,000 \times 0.25 = 0 + 250 + 250 = 500$$

Thus, in the above illustration, the total operating cycle has a real time duration of 10 seconds, with component 1 being pumped for the first 2.5 seconds of each cycle, component 2 being pumped for the next 2.5 seconds, and component 3 being pumped for the next 5 seconds of the operating cycle. The pumping of component 1 will be initiated at the count of 0, and the index values to initiate the pumping of components 2 and 3 are 250 and 500, respectively.

Where desired, the index value set into comparator 24 can be changed during a mixing operation to vary the proportions of the liquid components in the mixture. While variable composition control can be achieved by varying the composition manually during the mixing operation, as with thumb switches, it also can be automatically achieved by a device that varies the index value set into comparator 24 in accordance with a predetermined program. Referring again to the drawing, program controller 40 provides an analog output signal that varies in proportion to the desired index value to be set into comparator 24. The output of program controller 40 is electrically connected to analog/digital converter 42 by electrical conductor 44, which converts the analog signal to a corresponding digital signal, and the digital output is electrically connected to the index value set input of comparator 24 by conductor 46.

Program controller 40 can be any of the conventional devices of this type that develop a variable analog output signal in accordance with a predetermined program, which can be time dependent, i.e., the index value is varied as a function of lapsed time. One type of program controller is one which follows a profile scribed onto an electrically conducting plastic sheet. The programmer drives a potentiometer which, in conjunction with a power supply, produces a voltage proportional to the desired profile of proportions. This voltage is converted to a digital signal by analog/digital converter 42. This digital signal is used as the internal value stored in comparator 24. Thus, pump 14 delivers a continuously changing solvent composition which exactly matches the profile scribed on the plastic program sheet.

The invention is further described by the following example which is illustrative of a specific mode of practicing the invention and is not intended as limiting the scope of the invention as defined by the appended claims.

In this example, a series of 19 different mixtures of various proportions of water and 0.5 weight percent aqueous solution of benzyl alcohol are prepared using the apparatus of this invention substantially as illustrated in the drawing. An index value corresponding to desired concentration is set into the comparator. Samples of each of the produced mixtures are collected at the exit of the discharge conduit and analyzed to determine the proportion of the aqueous benzyl alcohol solution in the mixture. The results of these determinations are compared with the preselected concentration and the error calculated. These results are shown in the Table, and indicate that the proportion of the solvent mixture delivered compare quite favorably to the preselected proportion.

TABLE

| Run | Preselected Proportion (% of aqueous solution of benzyl alcohol) | Proportion Delivered (% of aqueous solution of benzyl alcohol) | Absolute Error (1) (% of aqueous solution of benzyl alcohol) | Relative Error (%) |
|---|---|---|---|---|
| 1 | 0.0 | 0.22 | 0.22 | — |
| 2 | 1.0 | 1.39 | 0.39 | 39. |
| 3 | 2.0 | 2.12 | 0.12 | 6.0 |
| 4 | 3.0 | 3.25 | 0.25 | 8.3 |
| 5 | 5.0 | 5.22 | 0.22 | 4.4 |
| 6 | 10.0 | 9.91 | −0.09 | −0.90 |
| 7 | 20.0 | 19.71 | −0.29 | −1.45 |
| 8 | 30.0 | 30.06 | 0.06 | 0.20 |
| 9 | 40.0 | 39.90 | −0.10 | −0.25 |
| 10 | 50.0 | 49.74 | −0.26 | −0.52 |
| 11 | 60.0 | 59.55 | −0.45 | −0.75 |
| 12 | 70.0 | 69.42 | −0.58 | −0.83 |
| 13 | 80.0 | 78.55 | −1.45 | −1.8 |
| 14 | 90.0 | 88.88 | −1.20 | −1.3 |
| 15 | 95.0 | 93.35 | −1.65 | −1.7 |
| 16 | 97.0 | 95.86 | −1.14 | −1.2 |
| 17 | 98.0 | 98.64 | 0.64 | 0.65 |
| 18 | 99.0 | 98.96 | −.04 | −0.04 |
| 19 | 99.9 | 98.96 | −.94 | −0.94 |

(1) Standard deviation = 0.74% aqueous solution of benzyl alcohol

While particular embodiments of the invention have been described, it will be understood, of course, that the invention is not limited thereto since many modifications can be made and it is intended to include within the invention such modifications as are within the scope of the claims.

The invention having thus been described, we claim:

1. An apparatus for mixing a plurality of liquid components in pre-selected proportions to form a mixture of said liquid components having a desired composition, which comprises:
   a plurality of liquid component storage reservoirs at least one of said reservoirs being available for each of the liquid components of said mixture;
   a pump for withdrawing liquid component from said plurality of reservoirs;
   switching means for successively connecting the suction of said pump to each of said plurality of liquid reservoirs;
   a conduit connected to the discharge of said pump for delivering said liquid mixture to a point of use;

pulse generating means to generate a series of constant frequency electrical pulses;

a digital counter electrically connected to the output of said pulse generating means for counting the number of pulses emitted from said pulse generating means during each operating cycle, said digital counter having a binary coded decimal output;

comparator means electrically connected to the output of said digital counter for comparing the number of pulses registered on said digital counter with an adjustable, pre-selected value; and electrical output means electrically connected to the output of said comparator means responsive to a signal from said comparator means for actuating said switching means to switch the suction of said pump from one of said liquid reservoirs to another of said reservoirs when the number of pulses registered on said digital counter equals the pre-selected value set into said comparator means and to reconnect the suction of said pump to the original reservoir at the start of each operating cycle;

whereby liquid components are successively pumped from each of said reservoirs for individually controlled short time intervals and admixed to provide a mixture of said components having the desired composition.

2. The apparatus defined in claim 1 wherein said pulse generating means includes means for adjusting the frequency of the pulse output to permit adjustment of the time span of said operating cycle.

3. The apparatus defined in claim 1 wherein said pulse generating means is a variable frequency square wave signal generator.

4. The apparatus defined in claim 1 wherein said pulse generating means is a pulse timer.

5. The apparatus defined in claim 1 including programming means to adjust the pre-selected value in said comparator means to vary the proportions of said liquid components in said mixture in accordance with a predetermined program.

6. The apparatus defined in claim 1 having two liquid component reservoirs, and wherein said switching means is adapted to alternately connect the suction of said pump to each of said reservoirs once during each operating cycle.

7. The apparatus defined in claim 6 wherein the switching means is a three-way solenoid valve.

8. The apparatus defined in claim 1 in combination with a liquid chromatograph having a chromatograph column, and wherein said conduit is connected to the inlet of said chromatograph column.

9. The apparatus defined in calim 1 wherein the capacity of said pump is such that the volume of liquid components pumped during each operating cycle is small as compared to the combined fluid volume of said pump and the common suction and discharge conduits to which it is connected.

10. An apparatus for supplying a solvent mixture of two liquid components in pre-selected proportions, which comprises:

first and second liquid component storage reservoirs for separately storing said liquid components;

a pump for withdrawing liquid component from said first and second reservoirs, the capacity of said pump being such that the volume of liquid components pumped during each operating cycle is small as compared to the combined fluid volume of said pump and the common suction and discharge conduits to which it is connected;

switching means for alternately connecting the suction of said pump to each of said first and second liquid reservoirs;

a conduit connected to the discharge of said pump for delivering said liquid mixture to a point of use;

pulse generating means to generate a series of constant frequency electrical pulses;

a digital counter electrically connected to the output of said pulse generating means for counting the number of pulses emitted from said pulse generating means during each operating cycle, said digital counter having a binary coded digital output;

comparator means electrically connected to the output of said comparator means for comparing the number of pulses registered on said digital counter with an adjustable, pre-selected value; and electrical output means electrically connected to the output of said comparator means responsive to a signal from said comparator means for actuating said switching means to switch the suction of said pump from one of said liquid reservoirs to the other of said reservoirs when the number of pulses registered on said digital counter equals the pre-selected value set into said comparator means and to reconnect the suction of said pump to the original reservoir at the start of each operating cycle as measured by a value of zero being registered on the digital counter; whereby liquid components are successively pumped from each of said reservoirs for individually controlled short time intervals and admixed to provide a solvent mixture of said components having the desired composition.

11. The apparatus defined in claim 10 wherein said pulse generating means includes means for adjusting the frequency of the pulse output to permit adjustment of the time span of said operating cycle.

12. The apparatus defined in claim 10 wherein said pulse generating means is a variable frequency square wave signal generator.

13. The apparatus defined in claim 10 wherein said pulse generating means is a pulse timer.

14. The apparatus defined in claim 10 including programming means to adjust the pre-selected value in said comparator means to vary the proportions of said liquid components in said mixture in accordance with a predetermined program.

15. The apparatus defined in claim 10 in combination with a liquid chromatograph having a chromatograph column, and wherein said conduit is connected to the inlet of said chromatograph column.

16. The apparatus defined in claim 10 wherein said switching means is a three-way solenoid valve.

17. An apparatus for use with a liquid chromatograph for supplying a solvent mixture of two liquid components in pre-selected proportions for use as the mobile phase in the liquid chromatograph, which comprises:

first and second liquid component storage reservoirs for separately storing said liquid components;

a pump for withdrawing liquid component from said first and second liquid component reservoirs, the capacity of said pump being such that the volume of liquid pumped during each operating cycle is small as compared to the combined fluid volume of said pump and the discharge conduit to which it is connected;

switching means for alternately connecting the suction of said pump to each of said first and second liquid component reservoirs;

a conduit connected to the discharge of said pump and adapted for connection to the inlet of the chromatograph column of a liquid chromatograph for delivering the solvent mixture to said chromatograph;

pulse generating means for generating a series of constant frequency electrical pulses, said means including means for adjusting the frequency of the pulse output to permit adjustment of the time span of said operating cycle;

a digital counter electrically connected to the output of said pulse generating means for counting the number of pulses emitted from said pulse generating means during each operating cycle, said digital counter having a binary coded decimal output;

comparator means electrically connected to the output of said digital counter for comparing the number of pulses registered on said digital counter with an adjustable pre-selected value; and electrical output means responsive to a signal from said comparator means for actuating said switching means to connect the suction of said pump to the other of said reservoirs when the number of pulses registered on said digital counter equals the pre-selected value set into said comparator means and to reconnect the suction of said pump to the original reservoir at the start of each operating cycle.

18. The apparatus defined in claim 17 wherein said pulse generating means is a variable frequency square wave signal generator.

19. The apparatus defined in claim 17 wherein said pulse generating means is a pulse timer.

20. The apparatus defined in claim 17 including programming means to adjust the pre-selected value in said comparator means to vary the proportions of said liquid components in said mixture in accordance with a predetermined program.

21. The apparatus defined in claim 17 wherein said digital counter counts from 0 to 999 and then repeats, and wherein the pre-selected value entered into said comparator means is an integer between 0 and 999, inclusive.

* * * * *